US009974847B2

(12) United States Patent
Bourinbaiar et al.

(10) Patent No.: US 9,974,847 B2
(45) Date of Patent: May 22, 2018

(54) TREATMENT AND PREVENTION OF TUBERCULOSIS

(75) Inventors: Aldar Bourinbaiar, College Park, MD (US); Vichai Jarathitikal, College Park, MD (US)

(73) Assignee: IMMUNITOR USA, INC., College Park, MD (US)

( * ) Notice: Subject to any disclaimer, the term of this patent is extended or adjusted under 35 U.S.C. 154(b) by 896 days.

(21) Appl. No.: 12/897,140

(22) Filed: Oct. 4, 2010

(65) Prior Publication Data

US 2011/0081382 A1 Apr. 7, 2011

Related U.S. Application Data

(60) Continuation-in-part of application No. 12/102,564, filed on Apr. 14, 2008, now Pat. No. 7,838,006, which is a division of application No. 09/935,344, filed on Aug. 23, 2001, now abandoned.

(60) Provisional application No. 60/227,520, filed on Aug. 24, 2000.

(51) Int. Cl.
*A61K 39/04* (2006.01)
*A61P 31/06* (2006.01)
*A61K 45/06* (2006.01)
*A61K 9/20* (2006.01)
*A61K 39/00* (2006.01)

(52) U.S. Cl.
CPC ............ *A61K 39/04* (2013.01); *A61K 9/2009* (2013.01); *A61K 9/2063* (2013.01); *A61K 2039/51* (2013.01); *A61K 2039/521* (2013.01); *A61K 2039/541* (2013.01); *A61K 2039/542* (2013.01); *A61K 2039/60* (2013.01)

(58) Field of Classification Search
None
See application file for complete search history.

(56) References Cited

U.S. PATENT DOCUMENTS

| | | | |
|---|---|---|---|
| 3,060,094 A | 10/1962 | Dutcher et al. | |
| 3,859,168 A | 1/1975 | Barth et al. | |
| 4,568,542 A | 2/1986 | Kronenberg | |
| 4,695,454 A | 9/1987 | Prince et al. | |
| 4,724,144 A * | 2/1988 | Rook ..................... | A61K 39/04 424/248.1 |
| 5,035,898 A * | 7/1991 | Chang ................... | A61K 9/2081 424/474 |
| 5,506,271 A | 4/1996 | Meruelo et al. | |
| 5,709,995 A | 1/1998 | Chisari et al. | |
| 5,830,475 A * | 11/1998 | Aldovini ................ | A61K 39/04 424/200.1 |
| 5,994,083 A | 11/1999 | Felici et al. | |
| 6,024,953 A | 2/2000 | Lathe et al. | |
| 6,245,532 B1 | 6/2001 | Smith et al. | |
| 6,383,806 B1 | 5/2002 | Rios | |
| 6,515,028 B1 | 2/2003 | Mueller et al. | |
| 6,544,528 B1 | 4/2003 | Yamamoto | |
| 6,623,764 B1 | 9/2003 | Sokoll et al. | |
| 6,635,246 B1 | 10/2003 | Barrett et al. | |
| 7,838,006 B2 | 11/2010 | Jirathitikal et al. | |
| 2002/0001595 A1 | 1/2002 | Sonntag et al. | |
| 2003/0143221 A1 | 7/2003 | Loibner et al. | |
| 2009/0226489 A1 | 9/2009 | Jira et al. | |

FOREIGN PATENT DOCUMENTS

| | | |
|---|---|---|
| EP | 0775494 | 5/1997 |
| JP | 57175127 | 10/1982 |
| WO | 9714434 | 4/1997 |
| WO | 0024420 | 5/2000 |
| WO | 0047222 | 8/2000 |

OTHER PUBLICATIONS

Cho et al. (Bull, WTO, 1956, vol. 14, p. 657-669).*
Denis et al. (Molecular Immunology, 2003, vol. 279-286).*
Lagranderie et al. (Vaccine, Jan. 2000, p. 1186-1195).*
Lagranderie et al. (Journal of Virology, 1997, p. 2303-2309).*
Dlugovitzky et al. (Immunotherapy, Mar. 2010, vol. 2, p. 159-169), Abstract only, one page attached.*
Pontisso et al., "Coinfection by Hepatitis B Virus and Hepatitis C Virus," Antiviral Therapy, vol. 3 Supplement 3, pp. 137-142 (1998—Abstract only).
Hepatitis C Vaccine Delivered by Inovio Biomedical's Electroporation System Shows Increased T-Cell Responses and Reduced Viral Loads, Study, Medical News Today, Jul. 4, 2008, Article URL: http://www.medicalnewstoday.com/articles/113964.php.
DNA-based Therapeutic Vaccine for Hepatitis C Posts Encouraging Results, Hepatitis Central, Apr. 29, 2009, URL for Article Source: http://www.biologynews.net/archives/2009/04/23/first_evidednce_for_dnabased_vaccination_against_chronic_hepatitis_c.html.
Shirai et al., "An Epitope in Hepatitis C Virus Core Region Recognized by Cytotoxic T Cells in Mice and Humans," Journal of Virology, vol. 68 No. 5, pp. 3334-3342 (May 1994).
Batdelger et al., "Open Label Trial of Therapeutic Hepatitis B Vaccine V-5 Immunitor (V5) Delivered by Oral Route," Letters in Drug Design & Discovery, vol. 4 No. 8, pp. 540-544 (Dec. 2007).
Berzofsky et al., "Progress on New Vaccine Strategies Against Chronic Viral Infections," Journal of Clinical Investigation, vol. 114 No. 4 pp. 450-462 (Aug. 2004).
C. Henderson (publisher), "Hypericin Profile to Potentially Include Hepatitis C and HIV," AIDS Weekly, Apr. 24, 1995, pp. 7-8.
Huang et al., "Recent Development of Therapeutics for Chronic HCV Infection," Antiviral Research, vol. 71 Nos. 2-3, pp. 351-362 (Sep. 2006).
Hughes et al., "Isolation and Immunizations with Hepatitis A Viral Structural Proteins: Induction of Antiprotein, Antiviral, and Neutralizing Responses," Journal of Virology, vol. 55 No. 2, pp. 395-401 (Aug. 1985).

(Continued)

*Primary Examiner* — Agnieszka Boesen
(74) *Attorney, Agent, or Firm* — Leason Ellis LLP

(57) ABSTRACT

The invention is within the field of immunology and microbiology, more specifically the field of mycobacteriology and is related to immunotherapy and prophylaxis of tuberculosis and related diseases. The composition useful for these purposes is disclosed, including the methods of using said composition.

2 Claims, No Drawings

(56) References Cited

OTHER PUBLICATIONS

Koziel et al., "Hepatitis C Virus (HCV)-Specific Cytotoxic T Lymphocytes Recognize Epitopes in the Core and Envelope Proteins of HCV," Journal of Virology, vol. 67 No. 12, pp. 7522-7532 (Dec. 1993).
Prince et al., "Strategies for Evaluation of Enveloped Virus Inactivation in Red Cell Concentrates Using Hypericin," Photochemistry and Photobiology, vol. 71 No. 2, pp. 188-195 (Feb. 2000).
Rascanelli et al., "Presentation of HCV Antigens to Naive CD8+T Cells: Why the Where, When, What and How are Important for Virus Control and Infection Outcome," Clinical Immunology, vol. 124 No. 1, pp. 5-12 (E-pub May 2007).
Rollier et al., "Control of Heterologous Hepatitis C Virus Infection in Chimpanzees is Associated with the Quality of Vaccine-Induced Peripheral T-Helper Immune Response," Journal of Virology, vol. 78 No. 1, pp. 187-196 (Jan. 2004).
Tan et al., "Strategies for Hepatitis C Therapeutic Intervention: Now and Next," Current Opinion in Pharmacology, vol. 4 No. 5, pp. 465-470 (Oct. 2004).
Batdelger et al., "Open-Label Trial of Therapeutic Immunization with Oral V-5 Immunitor (V5) Vaccine in Patients with Chronic Hepatitis C," Vaccine, vol. 26 No. 22, pp. 2733-2737 (May 2008).
Butov, et al., "Adjunct Immunotherapy in Patients with First-Diagnosed Tuberculosis, Relapsed TB, and Multi-Drug Resistant TB," 10 pages.
Arjanova et al., "Phase 2 Placebo Controlled Trial of V-5 Immunitor Adjunct Immunotherapy in Patients with TB, MDR-TB and HIV-TB," 16 pages.
Arjanova et al., "Phase 2 Trial of V-5 Immunitor (V5) in Patients with Chronic Hepatitis C Co-Infected with HIV and *Mycobacterium* Tuberculosis," Journal of Vaccines & Vaccination, vol. 1, Issue 1.1000103, 5 pages.
Lelie et al., Journal of Medical Virology, vol. 23, pp. 297-301 (1987).
Eisenthal et al., Viral Immunology, vol. 11, pp. 137-145 (1998).
Wladman et al., American Journal of the Medical Sciences, vol. 292, pp. 367-371 (1986).
Avtushenko et al., Journal of Biotechnology, vol. 44, pp. 21-28 (1996).
Moldoveanu et al., Journal of Infectious Diseases, vol. 167, pp. 84-90 (1993).
Definition of "immunogen", The On-Line Medical Dictionary, cancerweb.ncl.ac.uk/omd/.
Jirathitikal et al., HIV Cin Trials 2002;3(1): 21-26.
Jirathitikal et al., Electronic Journal of Biotechnology ISSN: 0717-3458, vol. 6, No. 1, Apr. 15, 2003.
Jirathitikal et al., Vaccine 21 (2003) 624-628; Current Pharmaceutical Design, 2003, 9 (18): 1419-1431.
Bourinbaiar et al., Acta Virologica 48: 73-78, 2004.
Jirathitikal et al., European Journal of Clinical Nutrition (2004) 58, 110-115.
Jirathitikal et al., Journal of Clinical Virology 744 (2004), 1-8.
Bourinbair et al., Viral Immunology 16(4), 2003, 427-445.
Epand et al., Biochem, J. (2002) 365, 841-848.
Definition "pill", Dorland's Illustrated Medical Dictionary, mercksource.com/pp/us/cns_health_library_frame.jsp?pg=/pp/us/cns/cns_hl_dorlands.jsp?pg=/pp/us/common/dorlands/dor_and/dmd_a-b_00.htm&cd=3d (indexed Aug. 2002).
Katakam et a., J Pharm Sci Jun. 1995 ; 84(6):713-6 (abstract only).
Meruelo et al., Therapeutic Agents with Dramatic Antiretroviral Activity and Little Toxicity at Effective Doses: Aromatic Polycyclic Diones Hypercin and Pseudohypericin, "Proceedings of the National Academy of Sciences," USA, vol. 85, No. 14, pp. 5230-5234 (Jul. 1988).
Miller, Alan L. "St. John's Wort (Hypericum perforatum): clinical effects on depression and other conditions," Alternative Medicine Review, vol. 3, No. 1, pp. 18-26 (Feb. 1998).
Diana Dlugovitzky et al., "Immunotherapy with oral, heat-killed, *Mycobacterium vaccae* in patients with moderate to advanced pulmonary tuberculosis", Immunotherapy (2010) 2(2), 159-169.
Micheline Lagranderie et al., "Oral Immunization with Recombinant *Mycobacterium bovis* BCG Simian Immunodeficiency Virus nef Induces Local and Systemic Cytotoxic T-Lymphocyte Responses in Mice", Journal of Virology, Mar. 1997, p. 2303-2309, vol. 71, No. 3.

* cited by examiner

TREATMENT AND PREVENTION OF TUBERCULOSIS

CROSS-REFERENCE TO RELATED APPLICATIONS

This application is a continuation-in-part of U.S. application Ser. No. 12/102,564 (filed on Apr. 14, 2008), which is a division of U.S. application Ser. No. 09/935,344 (filed on Aug. 23, 2001), which claims priority to U.S. provisional application 60/227,520 (filed Aug. 24, 2000), the disclosure of which is incorporated herein by reference.

FIELD OF THE INVENTION

The present invention relates to the therapy and prophylaxis of *mycobacterium*-induced infections such as tuberculosis or leprosy. In particular the invention relates to composition and methods of use thereof.

BACKGROUND OF THE INVENTION

Tuberculosis (TB) is a contagious disease caused predominantly by a bacterium called *Mycobacterium tuberculosis*. The bacteria mostly attack the lungs (pulmonary TB), but they can also attack the spine, brain, kidneys, and other organs or tissues. If not treated properly, TB can be fatal. There are 9.2 million new cases and 1.7 million deaths from TB annually. In addition, these intracellular bacteria are responsible for millions of cases of leprosy. Other debilitating diseases transmitted predominantly by intracellular agents include cutaneous and visceral leishmaniasis, American trypanosomiasis (Chagas disease), malaria, listeriosis, toxoplasmosis, histoplasmosis, trachoma, psittacosis, Q-fever, and Legionellosis including Legionnaires' disease. At this time, relatively little can be done to prevent debilitating infections in susceptible individuals exposed to these organisms. The first-diagnosed *Mycobacterium tuberculosis* infection is curable with the first line of anti-tuberculosis drugs (ATT) in over 90% of cases within 6 months.

However, when TB presents with HIV or there is a relapsing TB or drug-resistant form of TB, such as multi-drug resistant TB (MDR-TB) or extensively-drug resistant TB (XDR-TB), the currently available drugs are less effective and it takes as long as 12-24 months to treat a patient with success rate much lower than for drug-sensitive TB. According to various sources between one-third and one-half of patients with TB are infected with HIV, which is associated with very poor prognosis and high mortality. Treatment of TB patients with HIV co-infection is a challenging task. Despite the overwhelming burden of disease, no new anti-TB compounds were developed in last 40 years and current strains of TB are becoming increasingly resistant to existing drugs. At least 10% of TB cases are now drug-resistant forms. The treatment of TB, refractory to conventional ATT, requires the deployment of second line TB drugs. This represents a significant challenge, particularly in resource-poor countries, since the cost of the therapy increases 100-fold. It is clear that alternative and improved treatment options are needed. If such an intervention is found, the impact on the healthcare and clinical management of treatment-refractory, i.e., drug-resistant TB or relapsed TB and/or TB-HIV patients will be tremendous. The significant efforts are directed at finding new drugs and vaccines against TB. Immune-based interventions are actively sought as an adjunct therapy to conventional ATT.

The vaccine against TB was introduced in 1921 and consists of live Bacille Calmette Guerin (BCG)—a form of *mycobacterium* originally derived from *M. bovis*. BCG can reduce the risk of severe TB in young children but it is not very effective in preventing pulmonary TB in adolescents and adults, which are the populations with the highest rates of the disease. As BCG is not effective in these circumstances there are many attempts to develop better BCG-based recombinant vaccines (e.g. U.S. Pat. No. 5,830,475). BCG usually comes in injectable forms and is thus problematic for a widespread use, requiring specialized skills for delivery. Live BCG is also used as an oral vaccine. This is Brazilian liquid BCG vaccine, made by Fundação Ataulpho de Paiva (Brazilian League Against Tuberculosis) in Rio de Janeiro. It consists of unique 'Moreau Rio de Janeiro' strain of BCG. The strain has been established and used in Brazil for over 70 years. The effect of such oral vaccines is not predictable due to the potential danger of *mycobacterium* to revert to a virulent form, that can then cause the disease. Another unpredictable parameter recognized by those skilled in the art is that on passage to the stomach, the vaccine antigenic component(s) are rapidly inactivated by the gastric pH and digestive enzymes, and thus systemic assimilation through the gut wall is poor or non-existent.

TB vaccines were equally tried as therapeutic modalities for more than 100 years. Back in 1890, Robert Koch, the discoverer of *Mycobacterium tuberculosis*, had announced that the injection of tuberculin can cure the disease. However, the subsequent clinical trial involving nearly 2,000 patients revealed that only 2% benefited from this approach. There are reports of use of BCG as an adjunct to TB therapy. In a Chinese study involving 360 volunteers with TB, the negative sputum conversion rate in BCG recipients was 98.3% and 97.2% in chemotherapy control. While this was not significant, the recurrence of TB after 5 years in BCG group was 2.3%, but 6.9% in control group. In contrast, when therapeutic vaccination with BCG was attempted in a mouse model, it resulted in an exacerbation of the disease—a phenomenon first observed by Koch.

The therapeutic vaccine that has shown more promise is a killed *Mycobacterium* vaccae preparation which was discovered and developed by John Stanford (U.S. Pat. No. 4,724,144). This immunotherapy has been tested in many countries worldwide and usually resulted in a better outcome than chemotherapy alone. For example, negative sputum conversion seen in MDR-TB patients after 3 months was 43%, while among those who received chemotherapy was 21%. *M. vaccae* appeared to produce a measurable improvement in some geographical regions, but not in others, suggesting that different environmental and immunological experiences of the treated host can contribute to this inconsistency. Recently, a therapeutic vaccine, RUTI, containing detoxified cellular fragments of *M. tuberculosis*, was reported, but no data regarding its efficacy in humans is yet available, although in animals this vaccine has shown promising results. Other *mycobacterium* species were employed in attempt to treat TB. These included *M. phlei* and M. w (a vaccine originally developed for leprosy). Again, the clinical outcome in TB patients was modest and unpredictable. Due to potential risk of inducing a Koch-like reaction, there is a consensus among those skilled in the art that extreme caution is needed in order to develop safe and effective post-exposure vaccines.

Thus, there remains a long-felt need for better therapies or a vaccine. Such therapies additionally need to be free of undesirable properties, such as patient toxicity or even death, the inducement of drug resistance, and the requirement of complicated routes or means of delivery. While many promising vaccines were claimed to be successful in animal models, as a rule, they were not proven be effective and safe in humans. Thus, it is not obvious whether one will be able to develop an effective TB vaccine.

Currently 13 new candidate vaccines have entered clinical trials in humans and over 40 are in the pipeline. The overwhelming majority, if not all of these vaccines, are planned to be administered by injection because it is generally believed that oral administration of a vaccine leads to its destruction in the digestive tract. Thus, none of the present strategies teach, disclose, or suggest an oral composition comprising mycobacterial pathogen or a plurality of antigens of a pathogen or a fragment of a mycobacterial antigen along with an alloantigen.

SUMMARY OF THE INVENTION

The present invention describes an oral vaccine in a form of a tablet or pill comprising a pathogenic antigen, e.g., mycobacterial antigen, and antigen from pathogen-infected or non-infected tissue derived same species as the host itself (an allogeneic component or alloantigen). These are formulated into a pill having as carrier a metal salt. The composition of the invention overcomes the difficulties inherent in prior delivery systems and serves to introduce a health modifying agent, i.e., vaccine, into and across the mucosal membrane of a human or animal subject. The composition of the invention is administered through a mucosal surface, e.g., enterally by an oral route, to provide significant clinical benefit to subjects in need thereof.

The present invention departs from generally held beliefs that sophisticated compositions are necessary to overcome the lack of progress in developing effective immunotherapy and prophylaxis of mycobacterial diseases. The present invention features a surprising discovery that hydrolyzed *mycobacterium* antigens are not inferior in their clinical efficacy than heat-inactivated bacterial antigens. Thus, this composition can be regarded as a vaccine for treatment or prevention of a *mycobacterium* infection.

Another feature that enhances the attractiveness of the instant discovery is that the claimed composition is effective in oral dosage form. To be biologically available, an antigen of the instant invention is embedded or entrapped within pharmaceutically acceptable matrix. Furthermore, no immune adjuvant is required to produce the desired effect when the composition is administered orally.

In one aspect, this invention comprises a solid oral composition comprising a therapeutically effective amount of a hydrolyzed antigen, wherein said hydrolyzed antigen is derived from a body fluid of a donor infected with a *mycobacterium*. The solid oral composition is conveniently made into a tablet or pill. The body fluid can comprise a *mycobacterium* or *mycobacterium* antigen(s). This composition further comprises an alloantigen or xenoantigen that are embedded into a matrix such a metal salt. In another more general aspect of the invention the instant composition comprises an acid-hydrolyzed antigen, an alloantigen, or combination thereof embedded in a metal matrix.

Hydrolyzed antigens can be used as an immunotherapy or as a prophylactic preparation. Specifically, this invention relates to a composition, and methods of making and using said composition.

A further aspect of the present invention is a composition comprising both an alloantigen and a *mycobacterium* antigen. This is another feature that contributes to the surprising aspect of the present invention. A preferred embodiment of this feature is a solid composition comprising an acid-hydrolyzed alloantigen embedded in an orally available metal salt matrix, wherein the alloantigen or xenoantigen is a human alloantigen embedded in a divalent metal salt matrix and preferably heat-treated. The preferred administration of such a composition is oral.

Thus, a preferred feature of the present invention is that the composition is preferably in solid oral form such as a tablet or pill.

Yet another aspect of the present invention is a process of making the instant composition, which in general comprises hydrolyzing a *mycobacterium*, a fragment of a *mycobacterium*, or an alloantigen, embedding the hydrolysate into a solid matrix, and formulating the matrix into a composition for oral administration.

In another aspect of this invention hydrolyzed antigens are heat treated to render the instant composition safe and kill any remaining, un-hydrolyzed, adventitious pathogens which may become a source of infection. While this step is important, it is not critical, since the process of hydrolysis and embedding is accomplished at substantially elevated temperature, at least 56° C., preferably higher than 80° C., and for prolonged periods of time such as longer than 2 hours.

In another aspect of the invention, the composition is administered without an immune adjuvant.

While it is contemplated that the composition is derived from body organs or body fluids like whole blood, or plasma or serum, the present invention also anticipates a recombinant *mycobacterium* and antigens thereof such as those well known in the art and medical literature references. These can be mycobacteria grown in culture or they can be recombinant forms. The recombinant organisms or parts thereof can comprise naturally occurring sequences of amino acids or nucleic acids that constitute such antigens, derivatives of naturally occurring sequences that are substantially similar to a naturally occurring sequence, or sequences that mimic them either in linear or tertiary forms of, and chimeric sequences that may have more than one *mycobacterium*, such as for example BCG and *M. tuberculosis* within one composition. These and other permutations of various forms of a vaccine are contemplated without restriction and well known in the art.

A further aspect of the present invention embodies a method of treating a patient comprising the step of administering to the patient a therapeutically effective amount of hydrolyzed *mycobacterium*-infected cell, a *mycobacterium*, or fragment thereof. In addition to treating a patient infected with a *mycobacterium* or the present invention embodies a method of administering said vaccine prophylactically in order to reduce the likelihood or severity of eventual *mycobacterium* infection.

In an additional embodiment, the invention is directed to a method for eliciting an appropriate immune response (cellular or humoral) in a vertebrate subject comprising administering to a vertebrate subject a therapeutically effective amount of a selected macromolecule embedded into metal matrix of the invention.

The present invention also provides a method of reversing body weight loss caused by TB infection in a host, the method comprising administering the compositions of the present invention to the host.

The present invention also provides a method of reversing antituberculosis (ATT)-associated hepatotoxicity in a host caused by the administration of a conventional ATT therapy, the method comprising administering the composition of claim 1 to the host.

In a preferred embodiment, the vaccine is not subjected to any special modification aimed at enhancing the antigen "survival" in a hostile digestive milieu other than formulating with standard art-accepted excepients.

The innovative vaccine provides protection both by whole body immunity as well as in the critically important mucosal tissues, such as the eyes, lung, mouth, ear, gut, cervix, uterus, and rectum where a pathogen often first enters the body, e.g., spread by aerosol into person to be infected. In tests on animals and patients, the vaccines of the invention induce strong reactions by mucosal immune cells in the time frame required to stop infection. Thus, as oral vaccines, they perform at the mucosal surface and also stimulate systemic immunity by mounting immune response against the disease. The present invention provides a surprisingly effective and broadly applicable strategy for treating and preventing a variety of TB infections in diverse host organisms ranging from humans to other vertebrates who can succumb to mycobacterial infections.

Without limitation, the TB disease in humans and other animals can be caused by mycobacteria other than *M. tuberculosis*. This is due to the fact that all mycobacteria belong to the same class of pathogens, some of which are virulent and some are not. There are many known mycobacterial organisms including but not limited to BCG, *Mycobacterium* (*M.*) *tuberculosis, M. avium, M. habana, M. abscessus, M. aurum, M. bovis, M. vaccae, M. africanum, M. chelonae, M. fortuitum, M. fuerthensis, M. gastri. M. goodi, M. gordonae, M. immunogenum, M. intracellulare, M. paratuberculosis, M. lufu, M. kansasii, M. lentiflavum, M. leprae, M. w, M. mageritense, M. malmoense, M. rnarinum, M. massiliense, M. monacense, M. mucogenicum, M. neoaurum, M. peregrinum, M. phlei, M. porcinum, M. septicum, M. simiae, M. smegmatis, M. szulgai, M. terrae, M. tusciae, M. nonchromogenicum, M. ulcerans, M. chelonei, M. scrofulaceum, M. triviale, M. asciaticum, M. flavescens, M. genavense*, or *M. xenopi*. These mycobacteria can be propagated by art known methods by using liquid media, such as Middlebrook 7H9 or Saulton Synthetic Medium. The strains can be maintained as static or agitated cultures. Without limiting to whole pathogens one can utilize fragments thereof. The examples of such fragments are polypeptides derived from a bacterium belonging to the tuberculosis family, such as ESAT-6, TB10.4, CFP10, RD1-ORF5, RD1-ORF2, Rvl 036, MPB59, MPB64, MPB70, MPB83, MPT32, MPT64, Ag85B (MPT59), Ag85A, Ag85C, 19 kDa lipoprotein, and alpha-crystallin, or at least one T-cell epitope of any of the above mentioned antigens.

The invention is equally applicable to diseases caused by intracellular pathogens such as leprosy. Other similar diseases spread through the blood include cutaneous and visceral Leishmaniasis, Trypanosomiasis (Chagas disease), Toxoplasmosis, Histoplasmosis, Trachoma, Mycoplasma pneumoniae, Plasmodium falciparum (Malaria), Ureaplasma urealyticum, Mycoplasma genitalium, Legionellosis (Legionnaires' disease), Legionella pneumophilia, Yersinia pestis, Leptospirosis, Listeriosis, Rat-Bite Fever (Haverhill Fever), Streptobacillus moniliformis, Tick-Borne Diseases. Spirochetes: Borrelia burgdorferi, Erythema migrans, Acrodermatitis Atrophicans, Borrelial Lymphocytoma, Relapsing Fever, Ehrlichiosis, Tularemia. Chlamydia infections like Chlamydia pneumoniae, Chlamydia psittaci, Ornithosis, Psittacosis, Parrot Fever, Bartonella Infections, Q Fever, rickettsia infections such as Rocky Mountain Spotted Fever, Typhus, Epidemic Louse-Borne Scrub typhus, Treponema pallidum, Vibrio Infections and alike.

Heat-inactivated *mycobacterium* antigens are formulated into an oral pill suitable for effective vaccine administration to humans and animals. In addition to such an antigen, one needs an allogeneic antigen, i.e., alloantigen from the same species as the intended host but which is not mycobacterial antigen. A most convenient source of alloantigens is peripheral blood, but other sources can be deployed as well, including natural sources or recombinant sources or cell lines.

Furthermore, the preferred antigen is formulated into a pill that has as an excipient a metal salt. These salts are non-covalently bound to an antigen. Examples of salt of a representative metal, include, but are not limited to Aluminium magnesium boride, Calcium magnesium acetate, Dimagnesium phosphate, Magaldrate, Magnesium aluminide, Magnesium aspartate, Magnesium benzoate, Magnesium bromide, Magnesium carbonate, Magnesium chloride, Magnesium chloride hexahydrate, Magnesium citrate, Magnesium diboride, Magnesium diglutamate, Magnesium diuranate, Magnesium fluoride, Magnesium gluconate, Magnesium hexahydrate, Magnesium hydride, Magnesium hydroxide, Magnesium iodide, Magnesium lactate, Magnesium levulinate, Magnesium nitrate, Magnesium nitride, Magnesium orotate, Magnesium oxide, Magnesium oxychloride, Magnesium oxysulfate, Magnesium perchlorate, Magnesium peroxide, Magnesium phosphate, Magnesium pidolate, Magnesium silicide, Magnesium stearate, Magnesium sulfate, Magnesium sulfide, Magnesium sulfite, Magnesium trisilicate, Monomagnesium phosphate, Trimagnesium citrate and the like.

One skilled in the art can equally deploy salts resulting from reaction with other acids including but not limited to tosylate, methanesulfonate, acetate, citrate, malonate, tartarate, succinate, benzoate, ascorbate, alpha-ketoglutarate, alpha-glycerophosphate, formate, fumarate, propionate, glycolate, lactate, pyruvate, oxalate, oxychloride, maleate, salicyate, sulfate, sulfonate, nitrate, hydrobromate, hydrobromide, hydroiodide, and the like.

Generally, a salt of a metal can be: boride, acetate, phosphate, aluminide, aspartate, benzoate, bromide, carbonate, chloride, chloride hexahydrate, citrate, diboride, diglutamate, diuranate, fluoride, gluconate, hexahydrate, hydride, hydroxide, oxide, iodide, lactate, levulinate, nitrate, nitride, orotate, oxychloride, oxysulfate, perchlorate, peroxide, pidolate, silicide, stearate, sulfate, sulfide, sulfite, trisilicate, and the like.

In a further aspect of this invention two or more metals can be used simultaneously. For example, Calcium chloride and Magnesium chloride can be mixed at various acceptable ratios to which hydrolyzed antigens are embedded. Without limiting to dual metal sources it is clear that most sources contain small admixtures of plural metals or alloys thereof. For example magnesia can contain small quantities of calcium and other metals. Calcium in this mixture such as calcium carbonate does not interfere with the setting of the solid matter since higher proportion of reactive magnesia plays the predominant role. Reactive magnesium can be conveniently combined with other admixtures to create solid matters such as calcium aluminate, or other ingredients such as found for example in gypsum or cement-like compositions and that can be of significant advantage. In another embodiment naturally occurring minerals such as clay, kaolinite; chalk; silica; gypsum; feldspar; albite; anorthite; orthoclase; apatite; halite; calcite; dolomite; sodium carbonate; siderite; biotite; bentonite; muscovite; chlorite; stilbite; pyrite; hematite and alike that can be dispersed and made into a slurry into which antigen is admixed and hydrolyzed.

Compositions, methods for making vaccine compositions and methods of vaccinating or treating mammals/humans against tuberculosis are claimed. In particular, the present invention provides a method for protection of a non-infected mammal, including a human, from a TB infection, comprising administering to the non-infected mammal/human an effective amount of an oral vaccine formulation, which comprises a heat-inactivated TB infected cell, TB *mycobacterium*, or fragment thereof along with an alloantigen. Another method of the invention provides a method of treating of a TB infection, comprising administering to a mammal/human in need thereof an effective amount of an oral composition, said oral composition comprising a heat-inactivated TB infected cell, TB *mycobacterium*, or fragment thereof along with an alloantigen. The present invention also provides a method of producing an oral vaccine useful for the treatment or prevention of a TB bacilli-induced infection, comprising heat inactivating a tissue derived from a TB-infected animal, a TB bacterium, or fragment thereof and formulating into an oral composition with a metal salt.

DETAILED DESCRIPTION OF THE INVENTION

Administration of vaccines to non-infected hosts is referred to as "preventive vaccinating" while administration to already infected hosts is referred to as "therapeutic vaccination." The term "prevention" includes an attempt to halt the occurrence of a disease or disorder before it happens. The term "therapy" includes an attempt to alleviate the disease or clinical condition of an afflicted subject.

In the course of experimentations it has been discovered that when *Mycobacterium tuberculosis*, such as those found in the blood of one third of healthy people, are formulated into a tablet, such a preparation acquires biological activity in terms of inducing a more favorable clinical outcome when they are administered to individuals with tuberculosis or as means of prophylaxis of infection. The steps of making such a formulation are simple and straightforward. One of the steps is so-called hydrolysis, which can be easily achieved by acid treatment as the preferred mode of hydrolysis. The pH range is preferably below 6 and more preferably between 0.5 and 5.5, more preferably between 1 and 4, more preferably between 1.0 and 3.0, and even more preferably between 1.0 and 2.0. While these ranges are given as optimal ranges, they will not prevent one skilled in the art to determine additional ranges, which remain within the scope of the present invention. The proportion of hydrolyzed antigen, such as a protein, is at least 10% by weight of the non-hydrolyzed native antigen, preferably at least 20%, preferably at least 30%, preferably at least 40%, preferably at least 50%, preferably at least 60%, preferably at least 70%, preferably at least 80%, and can be at least 90%. The meaning of 100% hydrolyzation is a situation when all proteins are hydrolyzed to free amino acids without any larger residue, such as a peptide, remaining after the hydrolysis reaction.

The duration of hydrolysis can be anywhere between 5 minutes to several hours, more preferably they are between 10 minutes and 5 hours, even more preferably between 20 minutes and 3 hours. The duration can be a shorter period of hours, which is determined by simple experimentation under routine hydrolysis conditions well familiar to those skilled in the art. Thus, the duration of hydrolysis can be 30 minutes, one hour, 1.5 hours, 2 hours, 2.5 hours, or 3 hours, or intermediate times.

The acids that are useful for hydrolysis can be, but are not limited to, inorganic acids, such as hydrochloric acid, hydrobromic acid, sulfuric acid, nitric acid, carbonic acid, phosphoric acid and the like. Examples of organic acids include, but are not limited to, for example, acetic acid, citric acid, propionic acid, glycolic acid, pyruvic acid, oxalic acid, malic acid, malonic acid, succinic acid, maleic acid, fumaric acid, tartaric acid, benzoic acid, cinnamic acid, mandelic acid, methanesulfonic acid, ethanesulfonic acid, salicylic acid, p-toluenesulfonic acid, and the like.

The source of tuberculosis antigen does not necessarily need to be from blood or blood derivatives such as plasma or serum. Sputum or other body fluids like urine, gastrointestinal secretions, liquid of tissues or tumors, synovial fluid, saliva, sputum, cyst fluid, amniotic fluid, cerebrospinal fluid, peritoneal fluid, lung lavage fluid, semen, lymphatic fluid, tears, perspirations, and prostatic fluid may be used as a source of the tuberculosis antigen. These fluids can contain leukocytes, macrophages or other cells that are equally advantageous. Without limiting to fluids, solid tissues such as lung, liver, pancreas, skeletal muscle, heart, kidney, brain, bone marrow, tumor tissue, skin, myelin, collagen, feces, and other tissues may be used.

Whole blood, or serum or plasma, or culture broth with mycobacterial pathogen cells present in them or recombinantly obtained *mycobacterium* containing antigens are treated preferably with an acid or alkali. Cell lines like HeLa, for example, can be used equally to grow *mycobacterium*. One skilled in the art may use other hydrolyzing agents like enzymes or detergents. Samples to be hydrolyzed are pooled or from one individual, or maintained as a separate batch.

In one embodiment when the composition is still in liquid solution and in process of hydrolysis, the products of hydrolysis can be precipitated with a salt of a metal or with an alkaline metal hydroxide solution that forms a salt. This step effectively ends the hydrolysis since antigens are entrapped or embedded within the matrix of the solid matter and do not react with the hydrolytic agent. The precipitation can be run simultaneously with hydrolysis or started after the hydrolysis step, depending on the intended use of the final product. For example, an aqueous solution consisting of an antigen and alloantigen, preferably about 90% to about 20% protein, and more preferably about 80% to about 40% protein solution, is treated with an acid, until the pH is about 1 to about 6, preferably about 1 to about 4, more preferably about 1 to about 2. The solution is stirred at low speed, preferably at about 10 to about 500 rpm, more preferably about 30 to about 300, even more preferably about 60 to about 200 rpm for about 60 minutes to about 120 minutes, preferably about 45 to about 80 minutes, more preferably about 30 to about 60 minutes. A metal salt is then added to the stirring solution to create a slurry that solidifies as a solid mass. The mass is washed for about 1 minute to about 60 minutes, preferably about 5 to about 45 minutes, more preferably about 10 to about 30 minutes and then dried in an oven by heating at about 56 to about 200° C., preferably at about 70 to about 150° C., more preferably about 80 to about 140° C., more preferably about 100 to about 120° C., for about 1 hour to about 72 hours, preferably about 3 to about 48 hours, more preferably about 5 to about 12 hours. The dried solid mass is then reduced to a powder.

It is equally advantageous to start the precipitation and add hydrolyzant after that step. In yet another embodiment the metal salt is present prior to the hydrolysis and proteins are hydrolyzed in the presence of said metal salts, to be precipitated simultaneously and concomitantly. Representative steps for process of embedding an active ingredient such as an antigen together with alloantigen, or antigen alone without alloantigen, or alloantigen alone without the antigen, can include contacting the alloantigen with a metal salt solution to create a slurry and hydrolyzing the resulting mixture by contacting it with an acid so that this mixture is hardened and transforms into a solid phase or a solid state form—a process also know as a setting of the solid matter. This solid form is then reduced to powder particles embedded within active ingredient. The sequence of these steps are easily determined before hand and can be carried out without undue experimentation as long as the final product with active ingredient is clinically effective as determined by clinical studies.

The hydrolyzed mycobacterial antigens and alloantigens can be embedded in salts, including but not limited to: Lithium, Beryllium, Sodium, Silicone, Magnesium, Aluminium, Aluminum, Potassium, Calcium, Titanium, Vanadium, Chromium, Manganese, Cobalt, Nickel, Copper, Zinc, Arsenic, Zirconium, Molybdenum, Silver, Cadmium, Antimony, Barium, Osmium, Platinum, or Gold. Most suitable soluble salts include sodium chloride, potassium chloride, calcium chloride or magnesium chloride. An example of salt of a representative metal, such as for example magnesium, is Aluminium magnesium boride, Calcium magnesium acetate, Dirnagnesium phosphate, Magaldrate, Magnesium aluminide, Magnesium aspartate, Magnesium benzoate, Magnesium bromide, Magnesium carbonate, Magnesium chloride, Magnesium chloride hexahydrate, Magnesium citrate, Magnesium diboride, Magnesium diglutamate, Magnesium diuranate, Magnesium fluoride, Magnesium gluconate, Magnesium hexahydrate, Magnesium hydride, Magnesium hydroxide, Magnesium iodide, Magnesium lactate, Magnesium levulinate, Magnesium nitrate, Magnesium nitride, Magnesium orotate, Magnesium oxide, Magnesium oxychloride, Magnesium oxysulfate, Magnesium perchlorate, Magnesium peroxide, Magnesium phosphate, Magnesium pidolate, Magnesium silicide, Magnesium stearate, Magnesium sulfate, Magnesium sulfide, Magnesium sulfite, Magnesium trisilicate, Monomagnesium phosphate, Trimagnesium citrate and the like.

In a further aspect of this invention two or more metals can be used simultaneously. For example, Calcium chloride and Magnesium chloride can be mixed at various acceptable ratios into which hydrolyzed antigens are embedded. The difference between present composition and prior art compositions having an antigen mainly adsorbed to the surface of an immune adjuvant such as aluminum hydroxide is that the instant antigen is securely embedded within the matrix, which allows it to keep the physical structure intact even at conditions that are commonly unfavorable, i.e., high temperature at longer periods of time.

It is well known that exposure to high temperature, for example, heating at 56° C. or higher, like 80° C. for one hour or more is useful to destroy the adventitious pathogens, but not useful for making vaccines. However, surprisingly, the instant composition, when exposed to high temperatures has not lost its antigenicity and shows positive clinical benefit. Thus, instant composition can be safely used since potentially infectious virus that can be present within the composition is effectively killed by exposure to high temperatures for one hour or more. The advantage of thermal treatment, while obvious from the standpoint of elimination of infectious viruses, is not at all obvious from the standpoint of conservation of antigenicity—an observation that is contrary to the consensus prevailing in the art.

The instant composition is then combined with tablet excepients. An excepient is generally viewed as an inert substance which is added to an active ingredient to provide bulk, for example in tablets. These can be any of the following ingredients, or compounds of a similar nature: a binder such as microcrystalline cellulose, gum or gelatin; an excipient such as starch or lactose, a disintegrating agent such as alginic acid or corn starch; a lubricant such as magnesium stearate; a glidant such as colloidal silicon dioxide; a sweetening agent such as sucrose or saccharin; or a flavoring agent such as peppermint or some other flavoring. Mixing with excipients is performed by a wet or dry granulation processes well known to formulation experts and resulting mixture is compressed into tablets. Various properties of excipients, such as moisture content, particle size and distribution, polymorphism, amorphism, crystal habit, hydration state, and lubricant and binder level of the blend that have an influence on compaction are within routine knowledge of a practitioner. Tableting speed and mechanistic aspects of tableting such as choice of punches/dies, tableting machines can be selected without undue experimentation by artisans. In addition, dosages can contain various other materials which modify the physical form, for example, coatings of sugar, shellac, or other enteric agents. The tablets can be covered with enteric coating material that is predominantly soluble in the intestinal fluid, but substantially insoluble in the gastric fluids of stomach. Preferably enteric coating material is chosen from those that are commercially available, although new materials can be selected that are with the skill of practicing artisan.

The preferred dosage form is an oral solid dosage form such as a tablet or pill. Moreover, the pharmaceutical composition described herein can be formulated into any suitable dosage form, including but not limited to, aqueous oral dispersions, aqueous oral suspensions, aerosols, controlled release formulations, fast melt formulations, effervescent formulations, self-emulsifying dispersions, solid solutions, liposomal dispersions, lyophilized formulations, capsules, powders, delayed release formulations, immediate release formulations, modified release formulations, extended release formulations, pulsatile release formulations, multiparticulate formulations, mixed immediate release, controlled release formulations and the like.

In other embodiments of the present invention, the amount of active ingredient in the tablet, i.e., antigens with alloantigens, administered to a subject via a solid dosage form, such as a tablet or pill, is the amount known in the art to achieve a therapeutically effective concentration of drug of a human or animal in need thereof. For example, the amount of one or more active ingredients may range from about 0.0001 micrograms to about 1 g. In other embodiments, the amount of active ingredients may range from about 0.001 micrograms to about 100 mg. In other embodiments, the amount of active ingredients may preferably range from about 0.01 microgram to about 10,000 microgram, from about 0.5 microgram to about 1,000 microgram or from about 1 microgram to about 500 microgram. In another embodiment, a formulation is administered in a solid dosage form at a total protein concentration of about 10 microgram to about 500 microgram. In another embodiment, the active ingredients formulation is administered in a solid dosage form at concentration of about 1-100 microgram. In other embodiment the amount of active ingredients is from about 0.00001% to about 30% based on the total weight of the composition, preferably the amount is between about 0.001% and 20%, preferably the amount is between about 0.01% and 10%, preferably the amount is between about 0.1% and 5%. The content can also vary depending on the intended use. For therapeutic use, the content can be higher by about one order of magnitude from content of the composition intended for prophylactic use. For example, if in a therapeutic composition the quantity of mycobacterial antigen is 60 microgram, then in a prophylactic version the dose can be reduced to 5 or 10 micrograms. However, this is not an absolute requirement. These and other implications related to effective dose are not intended to be limiting and are provided by a way of example only. The precise amount of active ingredients that is "therapeutically effective" is determined by standard clinical testing whereby the clinical effect is monitored by means well known to those skilled in the art.

In a preferred embodiment, mycobacterial antigens are present in the composition together with alloantigen(s), which will be useful for prophylactic and therapeutic applications for preventing or actively treating tuberculosis. In the manufacture of most vaccines, considerable effort is made to purify vaccine antigens. This is due to the concern that when injected, antigens other than vaccine antigens cause undesirable immune reactions that can be sometimes life-threatening. Thus, calling for alloantigens to be present in the composition together with vaccine antigens is against common wisdom prevailing in the art. The ratio between mycobacterial antigens and alloantigen(s) is determined by art known methods. Preferably, the ideal ratio is one that is found naturally, as for example in the whole blood, i.e., the ratio between a quantity of mycobacteria and other host molecules such as the amount of total proteins found in the blood. The same applies to a situation in which antigen is recombinantly expressed in propagating cells, like yeast cells or mammalian cells such as CHO cells. In situations when composition components are grown in cells of species other than human but are intended to be used in humans, the alloantigen is then termed xenoantigen, which for purposes of this invention can be called alloantigen. Notwithstanding the above reasoning about a preferred ratio, one can deliberately increase the amount of alloantigen or antigen. In any case the amount of alloantigen shall not be too low so that it could be considered as a contaminant such as that found for example in standard vaccines, such as hepatitis B vaccine made from plasma. While the amount of contaminating plasma proteins, i.e., alloantigens, in hepatitis B vaccine made from pooled plasma varies depending on a batch or manufacturer it is usually less than 1%. In the case of hepatitis A vaccine the WHO recommends the amount of contaminating albumin to be less than 50 nanograms per dose. Thus, these requirements distinguish the instant composition from classical vaccine compositions of prior art, since in the present invention the ratio of various alloantigen molecules to antigen is always higher than 1:1, preferably more 10:1, ideally more than 100:1 and always exceeds 50 nanogram/gram when albumin is used to gauge the amount of allogeneic material. As intended here more than one type alloantigen is needed. Preferably one needs as wider diversity as possible. Such compositions, especially in oral form of delivery, will be useful to a host in need thereof, such as a human host or other species in need thereof.

In some embodiments, formulations provide a therapeutically effective amount of composition over an interval of about 3 hours to about 24 hours after administration, enabling, for example, once-a-day, twice-a-day (b.i.d.), or three times a day (t.i.d.) administration if desired. A simple dosing regimen of one or two tablets per day is preferred. Administration can be a single tablet administration, more preferably repeated administration for at least one week up to one month to one year, or carried out for years as deemed necessary. Treatment can be stopped after 1-3 months and repeated again after one month of break, although in some patients repeat treatment is not necessary for as long as 3 or 6 months intervals. In some instances, it is preferred to stop for one year and then repeat again. In some individuals treatment may not to be repeated at all as patients are cured and need no further dosing.

In another aspect of the invention the composition is administered without an immune adjuvant. While this is the preferred mode of administration, one skilled in the art, can administer the composition with an immune adjuvant known in the art. Examples of immune adjuvants include but not limited to bacterial adjuvants; cytokine adjuvants; plant-derived adjuvants and the like.

The composition of the present invention can be administered in combination with an anti-tuberculosis drug. Compositions/therapies of the instant invention may be used in combination with any other bioactive substances such as pharmaceutically effective substances, including, but not limited to, antiinflammatory drugs, analgesics, tranquillizers, antianxiety drugs, antispasmodics, antidepressants, antipsychotics, antianxiety drugs, narcotic antagonists, anti-parkinsonism agents, cholinergic agonists, chemotherapeutic drugs, immunosuppressive agents, antiviral drugs, antimicrobial drugs like antibiotics, appetite suppressants, anticholinergics, antimetrics, antihistaminics, antimigraine agents, coronary, cerebal or peropheral vasodilators, hormonal agents, contraceptives, antithrombotic agents, diuretics, antihypertensive agents, cardiovascular drugs, opioids, and the like.

Other features and advantages of the present invention are apparent from the additional detailed disclosure as provided below and which includes different examples. The examples provided below illustrate different components and methodology useful in practicing the present invention. The examples do not limit the claimed invention. Based on the present disclosure one skilled in the art can identify and employ other components and methodology to practice the present invention, which however are within the scope of the present invention.

EXAMPLES

Example 1

Upon analysis of results of phase 2 study of an oral, therapeutic hepatitis vaccine, over 94.4% of patients with chronic hepatitis C with concomitant TB and HIV had completely cleared bacilli in their sputum smears (Table 1). As a result 17 out 20 patients were discharged from the hospital within one month after treatment initiation. Statistical analysis by both parametric and non-parametric tests reveal that this phenomenon is highly significant. Once-daily vaccine tablet of the invention was administered per os to 20 patients for one month. Every patient who entered the study had enlarged liver and elevated hepatic damage markers, which at the end of study have improved in 19 out 20 (95%) patients. The reduction was highly significant, from $172.1 \pm 34$ to $18.2 \pm 28.2$ U/L ($P=5.0$ E-012) and $22.1 \pm 3.4$ to $10.9 \pm 2.5$ μmol/L ($P=5.7$ E-009) for ALT and total bilirubin respectively. Enlarged liver reduced from $3.5 \pm 1.4$ to $0.95 \pm 1.1$ cm above normal size ($P=2.9$ E-009). As patients were hospitalized in a TB hospital they were treated with standard anti-TB therapy (ATT). Surprisingly, vaccine compositions of the present invention appeared to contribute to higher and faster than expected sputum conversion rate;

94.4% of smear-positive patients became negative within one month. TB-associated fever subsided within mean/median 4.1/3 days; indicators of inflammation such as elevated erythrocyte sedimentation rate and high leukocyte counts returned back to normal from 32.3±11.4 to 9.9±6.4 mm/h (P=3.7 E-008) and 14.3±3.9 to 4.7±1.4×109 L (P=7.1 E-010) respectively. Average body weight gain was 7.7 kg (P=4.6 E-007) and hemoglobin levels increased from 114±7.1 to 123.4±6.6 g/L (P=1.4 E-007). No adverse events were observed at any time.

TABLE 1

Baseline and outcome characteristics of HCV-infected patients with HIV and TB co-infections treated with TB drugs in combination with vaccine for one month.

| No./Case No. | Sex | Age | TB drugs regimen | Months treated with ATT prior to vaccine | Smear Positive before | Smear Positive after | Liver size in cm over normal before | Liver size in cm over normal after | Erythrocyte sedimentation rate (ESR) before | Erythrocyte sedimentation rate (ESR) after |
|---|---|---|---|---|---|---|---|---|---|---|
| 1/602 | M | 33 | RZSE | 1 | − | − | 3 | 0 | 31 | 5 |
| 2/57 | F | 24 | HRZSE | 4 | + | − | 7 | 2 | 58 | 9 |
| 3/376 | M | 33 | HRZSE | 6 | + | − | 5 | 2 | 22 | 4 |
| 4/78 | M | 42 | HRZSE | 2 | + | − | 4 | 1 | 32 | 5 |
| 5/391 | M | 74 | HRZSE | 6 | + | − | 4 | 1 | 22 | 7 |
| 6/563 | F | 24 | HRZSE | 2 | + | − | 2 | 0 | 43 | 11 |
| 7/422 | M | 36 | HRZSE | 5 | + | + | 4 | 4 | 28 | 32 |
| 8/502 | M | 34 | HRZSE | 3 | + | − | 5 | 1 | 32 | 10 |
| 9/553 | M | 31 | HRZSE | 3 | + | − | 5 | 2 | 43 | 18 |
| 10/579 | F | 34 | HRZSE | 3 | + | − | 2 | 0 | 40 | 10 |
| 11/360 | M | 38 | HRZSE | 5 | − | − | 2 | 0 | 45 | 9 |
| 12/570 | M | 36 | HRZSE | 3 | + | − | 2 | 0 | 28 | 7 |
| 13/605 | M | 42 | HRZSE | 1 | + | − | 4 | 1 | 28 | 10 |
| 14/465 | F | 26 | HRZSE | 4 | + | − | 2 | 1 | 20 | 4 |
| 15/519 | M | 33 | HRZSE | 3 | + | − | 4 | 1 | 18 | 10 |
| 16/613 | M | 35 | HRZSE | 1 | + | − | 2 | 0 | 22 | 5 |
| 17/654 | M | 38 | HRZSE | 1 | + | − | 3 | 0 | 34 | 9 |
| 18/311 | M | 42 | HRZSE | 1 | + | − | 2 | 1 | 14 | 5 |
| 19/558 | F | 41 | HRZSE | 2 | − | − | 3 | 0 | 38 | 11 |
| 20/641 | M | 26 | HRZSE | 3 | + | − | 5 | 2 | 48 | 16 |
| 20 | 5/15 | 36.1 ± 10.6 | | Mean: 2.95 Median: 3 | 17 | 1 Fisher's exact 2-way test P < 0.000001 | 3.5 ± 1.4 Mean decrease 2.55 cm P = 2.893E−009 | 0.95 ± 1.1 | 32.3 ± 11.4 Mean decrease 22.4 P = 3.713E−008 | 9.9 ± 6.4 |

| No./Case No. | Leukocyte × 10⁹ L before | Leukocyte × 10⁹ L after | Hb g/L before | Hb g/L after | Weight change kg before | Weight change kg after | Total bilirubin μmol/L before | Total bilirubin μmol/L after | ALT IU/L before | ALT IU/L After |
|---|---|---|---|---|---|---|---|---|---|---|
| 1/602 | 4.3 | 3.8 | 114 | 129 | 57 | 66 | 20 | 10 | 235 | 12 |
| 2/57 | 11.6 | 4.3 | 101 | 118 | 62 | 75 | 25 | 10 | 162 | 12 |
| 3/376 | 18.3 | 6 | 112 | 125 | 68 | 79 | 18 | 12 | 162 | 12 |
| 4/78 | 14 | 6.8 | 118 | 128 | 74 | 86 | 13 | 15 | 235 | 12 |
| 5/391 | 12.3 | 2.8 | 120 | 132 | 72 | 82 | 25 | 10 | 162 | 10 |
| 6/563 | 12 | 3.4 | 108 | 115 | 49 | 59 | 20 | 10 | 162 | 12 |
| 7/422 | 14 | 3.8 | 112 | 110 | 62 | 54 | 20 | 20 | 162 | 138 |
| 8/502 | 20 | 6 | 108 | 116 | 67 | 74 | 25 | 10 | 162 | 12 |
| 9/553 | 12 | 6 | 120 | 132 | 71 | 83 | 25 | 10 | 162 | 12 |
| 10/579 | 14.9 | 4 | 112 | 120 | 47 | 52 | 25 | 10 | 162 | 12 |
| 11/360 | 12 | 4 | 118 | 122 | 75 | 83 | 20 | 10 | 235 | 12 |
| 12/570 | 19 | 5 | 122 | 128 | 60 | 70 | 25 | 10 | 162 | 12 |
| 13/605 | 18 | 4 | 104 | 118 | 66 | 75 | 25 | 10 | 162 | 12 |
| 14/465 | 18 | 3 | 118 | 128 | 62 | 67 | 20 | 10 | 132 | 12 |
| 15/519 | 9 | 4 | 118 | 120 | 69 | 73 | 20 | 10 | 132 | 12 |
| 16/613 | 14 | 4 | 112 | 128 | 71 | 75 | 25 | 10 | 162 | 12 |
| 17/654 | 14 | 8 | 122 | 130 | 68 | 77 | 25 | 10 | 162 | 12 |
| 18/311 | 18 | 6 | 128 | 132 | 70 | 75 | 25 | 10 | 162 | 12 |
| 19/558 | 18 | 4 | 112 | 118 | 59 | 70 | 20 | 10 | 235 | 12 |
| 20/641 | 13 | 6 | 102 | 118 | 77 | 85 | 20 | 10 | 132 | 12 |
| 20 | 14.3 ± 3.9 Mean decrease 9.6 × 10⁹ L P = 7.162E−010 | 4.7 ± 1.4 | 114 ± 7.1 Mean gain 9.3 g/L P = 1.419E−007 | 123.4 ± 6.6 | 65.3 ± 8.1 Mean gain 7.7 kg P = 4.604E−007 | 73 ± 9.6 | 22.1 ± 3.4 Mean decrease 11.2 μmol/L P = 5.679E−009 | 10.9 ± 2.5 | 172.1 ± 34 Mean decrease 153.9 IU/L P = 5.027E−012 | 18.2 ± 28.2 |

Following this discovery two clinical placebo-controlled studies were undertaken. These results are shown in Tables 2-5 and indicate unequivocally that claimed composition can indeed cure TB faster and more effectively regardless whether TB is drug-resistant or presents with HIV.

Example 2

In the clinical trial involving 55 patients only 1 (3.7%) and 3 (10.7%) subjects in vaccine and placebo arms had first-diagnosed, drug-sensitive TB; the remaining patients had retreated TB, MDR-TB, or HIV-TB. They were divided into immunotherapy (N=27) and placebo (N=28) arms matched by age, gender, baseline body weight, and clinical manifestations. After one month, 26 out 27 patients (96.3%) became sputum smear negative in vaccine group (P<0.0000001), whereas 7 out 28 (25%) in placebo group had converted (P=0.005). The vaccine composition of the present invention contributed to the downregulation of TB-associated inflammation as shown by the normalization of high leukocyte counts, erythrocyte sedimentation rate, and faster deffervescence than in the control. Patients in both arms experienced an equally significant increase in the level of hemoglobin corresponding to 128.9±17.6 vs 133.1±14.7 g/L (P=0.03) and 112.6±14 vs 117±11.7 g/L (P=0.03) in vaccine and placebo arms respectively. Nineteen out 28 (67.9%) placebo-receiving patients gained on average 1.07 kg (59.1±10 vs 60.1±10.4 kg; P=0.003). In contrast, every vaccine-treated patient gained mean 3.4 kg (59.7±8 vs 63.1±9 kg; P=5.7E-007). Clinical symptoms improved among all patients in the vaccine arm, while 28.6% of patients on placebo reported satisfactory results (P=0.007). No adverse or side effects attributable to the vaccine were seen at any time.

TABLE 2

Baseline and outcome characteristics of TB patients receiving vaccine in combination with ATT for one month

| No. | Sex | Age | TB form (* = HIV + status) | Months treated with ATT prior to vaccine | Therapy regimen | Hemoglobin g/L | | ERS (mm/h) | |
|---|---|---|---|---|---|---|---|---|---|
| | | | | | | before | After | before | after |
| 1 | M | 37 | Retreated | 3 | Individual | 140 | 155 | 16 | 30 |
| 2 | M | 33 | Retreated* | 1 | Individual | 138 | 136 | 15 | 11 |
| 3 | M | 33 | Retreated | 4 | Individual | 150 | 151 | 6 | 4 |
| 4 | M | 24 | MDR-TB | 12 | Individual | 110 | 122 | 15 | 9 |
| 5 | M | 35 | MDR-TB* | 2 | Individual | 149 | 150 | 7 | 8 |
| 6 | M | 47 | Retreated | 4 | Individual | 121 | 97 | 5 | 13 |
| 7 | M | 26 | MDR-TB | 9 | Individual | 146 | 142 | 17 | 5 |
| 8 | M | 59 | Retreated | 2 | Individual | 131 | 137 | 43 | 17 |
| 9 | M | 35 | Retreated | 1 | Individual | 152 | 150 | 3 | 4 |
| 10 | M | 45 | Retreated | 1 | Individual | 119 | 115 | 31 | 28 |
| 11 | F | 28 | Retreated* | 8 | Standard | 124 | 122 | 20 | 8 |
| 12 | M | 32 | Retreated* | 7 | Individual | 140 | 138 | 21 | 11 |
| 13 | F | 42 | Retreated* | 6 | Individual | 113 | 128 | 10 | 8 |
| 14 | M | 56 | 1stDx | 4 | Standard | 120 | 128 | 21 | 9 |
| 15 | M | 40 | Retreated | 3 | Standard | 124 | 126 | 28 | 4 |
| 16 | M | 33 | Retreated | 3 | Standard | 150 | 142 | 6 | 8 |
| 17 | M | 34 | Retreated | 2 | Standard | 145 | 143 | 6 | 7 |
| 18 | M | 55 | Retreated | 2 | Standard | 142 | 145 | 48 | 11 |
| 19 | M | 45 | Retreated | 4 | Individual | 124 | 143 | 18 | 4 |
| 20 | M | 41 | Retreated | 11 | Individual | 136 | 138 | 23 | 9 |
| 21 | M | 54 | Retreated | 3 | Standard | 117 | 125 | 21 | 11 |
| 22 | M | 32 | 1stDx* | 2 | Standard | 114 | 122 | 42 | 18 |
| 23 | M | 36 | MDR-TB | 4 | Individual | 142 | 148 | 12 | 8 |
| 24 | M | 23 | 1stDx* | 3 | Standard | 145 | 148 | 24 | 8 |
| 25 | F | 24 | 1stDx* | 4 | Standard | 101 | 118 | 58 | 9 |
| 26 | M | 42 | Retreated* | 1 | Standard | 104 | 118 | 28 | 10 |
| 27 | M | 37 | Retreated* | 1 | Standard | 84 | 108 | 47 | 11 |
| | 3/24 | Mean 38.1 ± 10 Median 36 | | Mean 4 ± 3 Median 3 | | 128.9 ± 17.6 P = 0.03 | 133.1 ± 14.7 | 21.9 ± 14.8 P = 0.0003 | 10.5 ± 6.4 |

| | Leukocyte count × 10⁹ L | | Smear positive | | Axillary temperature (° C.) | | Body weight (kg) | |
|---|---|---|---|---|---|---|---|---|
| No. | before | after | before | after | before | after | before | after |
| 1 | 8.7 | 7.2 | + | − | 38 | 36.8 | 58 | 60 |
| 2 | 6.7 | 4.1 | + | + | 38.3 | 36.8 | 60 | 61 |
| 3 | 5.2 | 4.8 | + | − | 37.8 | 36.8 | 65 | 70 |
| 4 | 11 | 8 | + | − | 38 | 36.8 | 55 | 57 |
| 5 | 9 | 8 | + | − | 37.6 | 36.8 | 60 | 61 |
| 6 | 11.3 | 3.7 | + | − | 37.8 | 36.8 | 55 | 57 |
| 7 | 6.1 | 6.4 | + | − | 38 | 36.8 | 42 | 45 |
| 8 | 8.1 | 7.8 | + | − | 37.3 | 36.8 | 57 | 59 |
| 9 | 12.4 | 10.8 | + | − | 37.4 | 36.8 | 63 | 65 |
| 10 | 7.9 | 11.3 | + | − | 37.9 | 36.8 | 50 | 51 |
| 11 | 7.1 | 5.1 | + | − | 36.8 | 36.8 | 53 | 58 |
| 12 | 14 | 6 | + | − | 36.8 | 36.8 | 63 | 68 |
| 13 | 6.9 | 6.1 | + | − | 38 | 36.8 | 50 | 55 |
| 14 | 5.9 | 5.3 | + | − | 38.3 | 36.8 | 48 | 50 |
| 15 | 12.2 | 7.4 | + | − | 37.1 | 36.8 | 65 | 66 |
| 16 | 5.2 | 5.6 | + | − | 37.1 | 36.8 | 65 | 66 |

TABLE 2-continued

Baseline and outcome characteristics of TB patients receiving vaccine in combination with ATT for one month

| | | | | | | | | |
|---|---|---|---|---|---|---|---|---|
| 17 | 16.7 | 6.3 | + | − | 37.8 | 36.8 | 58 | 60 |
| 18 | 11.5 | 7 | + | − | 37.4 | 36.8 | 67 | 69 |
| 19 | 9 | 5.9 | + | − | 36.8 | 36.8 | 71 | 79 |
| 20 | 7.7 | 5 | + | − | 37.8 | 36.8 | 73 | 78 |
| 21 | 12.8 | 8.1 | + | − | 36.8 | 36.8 | 50 | 55 |
| 22 | 6.3 | 7.1 | + | − | 37.4 | 36.8 | 59 | 63 |
| 23 | 7.8 | 7.2 | + | − | 38 | 36.8 | 67 | 71 |
| 24 | 8.6 | 4 | + | − | 37.3 | 36.8 | 69 | 73 |
| 25 | 11.6 | 4.3 | + | − | 38 | 36.8 | 62 | 75 |
| 26 | 18 | 4 | + | − | 38 | 36.8 | 66 | 75 |
| 27 | 11.6 | 9.2 | + | − | 38 | 37.2 | 56 | 58 |
| | 9.6 ± 3.4 | 6.5 ± 2 | 0/27 | 26/1 | 4/23 37.6 ± 0.48 | 27/0 36.8 ± 0.08 | 59.7 ± 8 | 63.1 ± 8.6 |
| | $P = 0.0002$ | | $P < 0.0001$ | | $P = 2.6E{-}009$ | | $P = 5.7E{-}007$ | |

TABLE 3

Baseline and outcome characteristics of TB patients receiving placebo in combination with ATT for one month

| No. | Sex | Age | Tb form (* = HIV + status) | Months treated with ATT prior to placebo | Therapy regimen | Hemoglobin (g/L) before | After | ESR (mm/h) before | after |
|---|---|---|---|---|---|---|---|---|---|
| 1 | M | 29 | Retreated* | 8 | Individual | 102 | 104 | 23 | 20 |
| 2 | M | 35 | Retreated* | 6 | Individual | 126 | 130 | 13 | 11 |
| 3 | M | 44 | Retreated | 2 | Standard | 108 | 112 | 14 | 10 |
| 4 | M | 35 | Retreated | 2 | Individual | 118 | 120 | 18 | 15 |
| 5 | M | 28 | MDR-TB | 4 | Individual | 120 | 132 | 32 | 11 |
| 3 | M | 24 | Retreated | 1 | Individual | 115 | 117 | 22 | 18 |
| 7 | M | 22 | Retreated | 1 | Standard | 121 | 122 | 28 | 24 |
| 8 | M | 44 | MDR-TB | 3 | Individual | 128 | 130 | 16 | 9 |
| 9 | F | 78 | 1st Dx | 3 | Standard | 116 | 124 | 14 | 9 |
| 10 | M | 28 | MDR-TB | 3 | Individual | 128 | 122 | 16 | 11 |
| 11 | F | 41 | 1st Dx | 3 | Standard | 113 | 122 | 21 | 10 |
| 12 | M | 41 | 1st Dx | 3 | Standard | 120 | 132 | 14 | 8 |
| 13 | M | 47 | Retreated | 4 | Standard | 126 | 132 | 24 | 10 |
| 14 | M | 44 | Retreated* | 4 | Standard | 118 | 128 | 18 | 9 |
| 15 | M | 33 | Retreated* | 3 | Individual | 100 | 103 | 22 | 16 |
| 16 | F | 21 | MDR-TB | 4 | Individual | 102 | 100 | 14 | 11 |
| 17 | M | 24 | MDR-TB | 10 | Individual | 110 | 112 | 15 | 10 |
| 18 | M | 30 | 1st Dx* | 1 | Standard | 112 | 110 | 26 | 22 |
| 19 | M | 33 | Retreated* | 2 | Individual | 116 | 108 | 15 | 12 |
| 20 | M | 31 | 1st Dx* | 3 | Standard | 122 | 120 | 17 | 15 |
| 21 | F | 50 | Retreated | 4 | Individual | 130 | 118 | 10 | 18 |
| 22 | F | 42 | Retreated | 1 | Individual | 83 | 90 | 38 | 35 |
| 23 | M | 51 | Retreated | 12 | Individual | 65 | 96 | 47 | 21 |
| 24 | M | 52 | Retreated | 1 | Individual | 110 | 112 | 26 | 20 |
| 25 | M | 53 | Retreated | 1 | Individual | 119 | 120 | 35 | 28 |
| 26 | M | 45 | Retreated | 1 | Individual | 117 | 115 | 18 | 9 |
| 27 | M | 36 | Retreated | 1 | Individual | 108 | 110 | 15 | 11 |
| 28 | M | 31 | Retreated | 4 | Individual | 100 | 135 | 21 | 27 |
| | 5/23 | Mean 38.3 ± 12 Median 35.5 | | Mean 3.4 ± 2.7 Median 3 | | 112.6 ± 14 | 117 ± 11.7 $P = 0.03$ | 21.1 ± 8.6 | 15.4 ± 7 $P = 7.9E{-}005$ |

| No. | Leukocyte count × 10$^9$ L before | after | Smear positive before | after | Axillary temperature (° C.) before | after | Body weight (kg) before | after |
|---|---|---|---|---|---|---|---|---|
| 1 | 17 | 17 | + | + | 38 | 37.8 | 60 | 60 |
| 2 | 11 | 8 | + | − | 38.3 | 36.8 | 68 | 70 |
| 3 | 9 | 8 | + | + | 37.8 | 37.4 | 61 | 62 |
| 4 | 12 | 11 | + | + | 38 | 37.5 | 69 | 70 |
| 5 | 12 | 9 | + | − | 37.6 | 36.8 | 68 | 72 |
| 3 | 8 | 9 | + | + | 37.8 | 37.6 | 70 | 71 |
| 7 | 14 | 11 | + | + | 38 | 37.4 | 67 | 67 |
| 8 | 9 | 8 | + | + | 37.3 | 36.8 | 72 | 73 |
| 9 | 8 | 8 | + | − | 37.4 | 36.8 | 52 | 54 |
| 10 | 13 | 9 | + | + | 37.9 | 36.8 | 60 | 61 |
| 11 | 12 | 8 | + | − | 36.8 | 36.8 | 47 | 50 |
| 12 | 9 | 5 | + | − | 36.8 | 36.8 | 78 | 81 |
| 13 | 11 | 6 | + | − | 38 | 36.8 | 72 | 71 |
| 14 | 13 | 8 | + | − | 38.3 | 36.8 | 61 | 63 |
| 15 | 11 | 10 | + | + | 37.1 | 37.7 | 57 | 57 |

TABLE 3-continued

Baseline and outcome characteristics of TB patients receiving placebo in combination with ATT for one month

| 16 | 9 | 8 | + | + | 37.1 | 37.2 | 47 | 48 |
|---|---|---|---|---|---|---|---|---|
| 17 | 11 | 9 | + | + | 37.8 | 37.5 | 55 | 55 |
| 18 | 7 | 9 | + | + | 37.4 | 38 | 63 | 63 |
| 19 | 11 | 10 | + | + | 36.8 | 37.4 | 60 | 55 |
| 20 | 8 | 8 | + | + | 37.8 | 37.4 | 65 | 65 |
| 21 | 7.8 | 7.5 | + | + | 37.3 | 37.5 | 55 | 56 |
| 22 | 7.7 | 8 | + | + | 37.5 | 36.8 | 35 | 36 |
| 23 | 9.4 | 9.2 | + | + | 38 | 36.8 | 58 | 60 |
| 24 | 5.5 | 6 | + | + | 38 | 37.5 | 55 | 55 |
| 25 | 11.2 | 12.3 | + | + | 37.3 | 37.1 | 40 | 41 |
| 26 | 11.5 | 9 | + | + | 37.5 | 37 | 55 | 55 |
| 27 | 16.4 | 12 | + | + | 38 | 37.3 | 49 | 50 |
| 28 | 5.1 | 7.8 | + | + | 37.5 | 37.1 | 55 | 57 |
| | 10.3 ± 2.9 | 9 ± 2.3 | 0/28 | 7/21 | 3/25 37.6 ± 0.4 | 11/17 37.2 ± 0.4 | 59.1 ± 9.9 | 60.1 ± 10.4 |
| | P = 0.002 | | P = 0.01 | | P = 0.0005 | | P = 0.003 | |

Example 3

In the third study conducted in 34 adult, there were 18 first-diagnosed (52.9%), 6 relapsed TB (17.6%), and 10 MDR-TB (29.4%) cases. The immunotherapy (N=24; Table 4) and placebo (N=10; Table 5) arms received once-daily tablet of vaccine or placebo in addition to conventional anti-TB therapy (ATT) administered under directly observed therapy (DOT). The enlarged liver, total bilirubin, erythrocyte sedimentation rate, lymphocyte and leukocyte counts improved significantly in vaccine recipients (P equal to 0.002; 0.03; 8.3E-007; 2.8E-005; and 0.002 respectively) but remained statistically unchanged in the placebo group (0.68; 0.96; 0.61; 0.91; and 0.43). The changes in hemoglobin and ALT levels in both treatment arms were not significant. The body weight increased in all vaccine-treated patients by an average 3.5±1.8 kg (P=2.3E-009), while 6 out 10 patients on placebo gained mean 0.9±0.9 kg (P=0.01). Mycobacterial clearance in sputum smears was observed in 78.3% and 0% of patients on vaccine and placebo (P=0.009). The conversion rate in vaccine-receiving subjects with MDR-TB (87.5%) seemed to be higher than in first diagnosed TB (61.5%) but the difference was not significant (P=0.62). Scoring of sputum bacillary load (range 0-3) at baseline and post-treatment revealed highly significant decrease in vaccine group (from mean/median 2.2/3 to 0.3/0; P=6E-010) but not in placebo (1.9/1.5 vs. 1.8/1; P=0.34). No adverse effects or TB reactivation were seen at any time during follow-up. Thus, the vaccine of the present invention is safe as an immune adjunct to chemotherapeutic management of TB and has a potential to shorten the duration of treatment.

TABLE 4

Baseline and outcome characteristics of TB patients receiving vaccine in combination with TB drugs for 30 days

| No./Case No. | Sex | Age | Months on ATT prior to vaccine | Dx | TB drugs regimen | Smear status before | Smear status after | Liver size in cm over normal before | Liver size in cm over normal after | Erythrocyte sedimentation rate (mm/h) before | Erythrocyte sedimentation rate (mm/h) after |
|---|---|---|---|---|---|---|---|---|---|---|---|
| 1/80 | M | 43 | 0 | 1$^{st}$Dx | HRZE | 3 | 1 | 2 | 0 | 50 | 30 |
| 2/146 | M | 39 | 0 | 1$^{st}$Dx | HRZE | 3 | 1 | 0 | 1 | 17 | 16 |
| 3/184 | M | 44 | 1 | 1$^{st}$Dx | HRZES | 1 | 0 | 1 | 0 | 21 | 15 |
| 4/34 | M | 60 | 3 | 1$^{st}$Dx | HRZES | 3 | 0 | 1 | 0 | 27 | 20 |
| 5/186 | F | 27 | 1 | 1$^{st}$Dx | HRZES | 3 | 2 | 1 | 0 | 58 | 40 |
| 6/165 | M | 26 | 3 | 1$^{st}$Dx | HRZES | 3 | 1 | 3 | 1 | 15 | 6 |
| 7/179 | M | 57 | 1 | 1$^{st}$Dx | HRZES | 2 | 0 | 0 | 0 | 32 | 9 |
| 8/225 | M | 31 | 0 | 1$^{st}$Dx | HRZES | 1 | 0 | 0 | 0 | 36 | 26 |
| 9/115 | M | 39 | 0 | 1$^{st}$Dx | HRZES | 2 | 1 | 0 | 0 | 50 | 30 |
| 10/805 | M | 31 | 3 | 1$^{st}$Dx | HRZES | 3 | 0 | 0 | 0 | 37 | 2 |
| 11/106 | M | 59 | 0 | 1$^{st}$Dx | HRZES | 1 | 0 | 1 | 1 | 25 | 24 |
| 12/65 | M | 26 | 0 | 1$^{st}$Dx | HRZES | 3 | 0 | 3 | 1 | 19 | 9 |
| 13/12 | M | 51 | 1 | 1$^{st}$Dx | HRZES | 3 | 0 | 1 | 2 | 15 | 6 |
| 14/192 | F | 46 | 1 | RTB | HRZES | 3 | 0 | 0 | 0 | 17 | 3 |
| 15/94 | F | 54 | 0 | RTB | RZEO | 3 | 0 | 3 | 1 | 16 | 8 |
| 16/177 | F | 35 | 1 | RTB | HRZEA | 3 | 0 | 0 | 0 | 32 | 15 |
| 17/5 | M | 49 | 1 | MDR | HRZEO | 3 | 0 | 1 | 1 | 55 | 40 |
| 18/755 | M | 29 | 9 | MDR | HEAOC | 3 | 1 | 5 | 3 | 25 | 14 |
| 19/866 | F | 53 | 2 | MDR | ZEPasAO | 0 | 0 | 0 | 0 | 19 | 17 |
| 20/139 | M | 29 | 0 | MDR | ZEPasAO | 2 | 0 | 1 | 0 | 10 | 8 |
| 21/807 | M | 29 | 4 | MDR | ZEPasAO | 2 | 0 | 3 | 0 | 25 | 17 |

TABLE 4-continued

Baseline and outcome characteristics of TB patients receiving vaccine in combination with TB drugs for 30 days

| 22/171 | M | 49 | 1 | MDR | ZEPasO | 1 | 0 | 2 | 0 | 24 | 17 |
|---|---|---|---|---|---|---|---|---|---|---|---|
| 23/156 | M | 52 | 0 | MDR | ZPasAO | 1 | 0 | 3 | 1 | 24 | 18 |
| 24/469 | M | 22 | 1 | MDR | CsCiGF | 1 | 0 | 0 | 0 | 23 | 18 |
| | 5/19 | Mean 40.8 ± 12 Median = 41 | Mean 1.6 ± 2.5 Median 1 | 1st Dx = 13 RTB = 3 MDR = 8 | | 1/232.2/3 P = 0.000027 | 18/60.3/0 | 1.3 ± 1.4/1 P = 0.0018 | 0.5 ± 0.8/0 | 28 ± 13.4 P = 8.3E−007 | 17 ± 10.4 |

| No./Case No. | Lymphocytes (%) | | Leukocyte count (×10$^9$/L) | | Hb (g/L) | | Weight change (kg) | | Total bilirubin (μmol/L) | | ALT | |
|---|---|---|---|---|---|---|---|---|---|---|---|---|
| | before | after | before | after | before | after | before | After | before | after | before | after |
| 1/80 | 18 | 23 | 11.7 | 9.2 | 129 | 122 | 64 | 65 | 8.8 | 8.8 | 0.4 | 0.1 |
| 2/146 | 28 | 25 | 4.4 | 5.4 | 142 | 139 | 65 | 66 | 9.9 | 8.8 | 0.2 | 0.6 |
| 3/184 | 19 | 29 | 6.1 | 5.6 | 127 | 116 | 74 | 78 | 8.8 | 9.9 | 0.6 | 0.5 |
| 4/34 | 29 | 31 | 6.1 | 6 | 144 | 122 | 71 | 74 | 8.8 | 8.8 | 0.7 | 0.1 |
| 5/186 | 16 | 22 | 11 | 8 | 101 | 110 | 43 | 49 | 8.8 | 8.8 | 0.7 | 0.7 |
| 6/165 | 30 | 37 | 11.6 | 6 | 158 | 140 | 66 | 69 | 8.8 | 12.1 | 0.9 | 1.7 |
| 7/179 | 21 | 34 | 5.3 | 5.1 | 109 | 123 | 60 | 63 | 12.1 | 9.9 | 0.1 | 0.5 |
| 8/225 | 21 | 29 | 7.5 | 6.6 | 134 | 136 | 62 | 68 | 8.8 | 9.9 | 0.3 | 0.4 |
| 9/115 | 14 | 17 | 11.7 | 9.6 | 154 | 144 | 63 | 67 | 8.8 | 8.8 | 0.2 | 0.2 |
| 10/805 | 33 | 46 | 9.7 | 4 | 145 | 151 | 64 | 67 | 9.9 | 8.8 | 0.4 | 0.4 |
| 11/106 | 27 | 29 | 6.6 | 5.2 | 138 | 136 | 61 | 66 | 18.1 | 12.1 | 0.3 | 0.5 |
| 12/65 | 24 | 21 | 5.7 | 6.0 | 156 | 153 | 70 | 73 | 8.8 | 8.8 | 1.3 | 0.7 |
| 13/12 | 16 | 29 | 14.2 | 6.9 | 142 | 150 | 81 | 81 | 12.1 | 8.8 | 0.6 | 0.9 |
| 14/192 | 17 | 21 | 8.3 | 7.7 | 103 | 110 | 52 | 58 | 8.8 | 8.8 | 0.3 | 0.1 |
| 15/94 | 24 | 34 | 6.1 | 5.1 | 143 | 128 | 58 | 59 | 8.8 | 8.8 | 1.2 | 0.6 |
| 16/177 | 18 | 37 | 6.7 | 5.5 | 142 | 136 | 62 | 67 | 8.8 | 8.8 | 0.2 | 0.2 |
| 17/5 | 18 | 37 | 20.4 | 7.5 | 138 | 100 | 73 | 75 | 12.1 | 9.9 | 0.8 | 0.8 |
| 18/755 | 11 | 26 | 7.9 | 7.9 | 129 | 138 | 59 | 62 | 8.8 | 8.8 | 0.5 | 0.9 |
| 19/866 | 35 | 31 | 4.4 | 5.8 | 139 | 167 | 55 | 59 | 14.3 | 10.4 | 0.3 | 0.4 |
| 20/139 | 33 | 35 | 10 | 6.2 | 147 | 148 | 65 | 69 | 8.8 | 8.8 | 0.6 | 0.6 |
| 21/807 | 26 | 37 | 10.1 | 6.8 | 135 | 133 | 57 | 60 | 9.9 | 8.8 | 1.3 | 0.6 |
| 22/171 | 12 | 26 | 5.3 | 4.9 | 159 | 137 | 72 | 74 | 14.2 | 9.9 | 1 | 0.6 |
| 23/156 | 24 | 26 | 5 | 4.2 | 124 | 128 | 68 | 73 | 13.5 | 8.8 | 1.4 | 0.7 |
| 24/469 | 25 | 27 | 19.6 | 7.2 | 121 | 131 | 66 | 73 | 8.8 | 8.8 | 0.1 | 0.2 |
| | 22.5 ± 6.8 P = 2.8E−005 | 29.5 ± 6.7 | 9 ± 4.3 P = 0.0024 | 6.4 ± 1.4 | 135.8 ± 15.8 P = 0.39 | 133.3 ± 15.5 | 63.8 ± 7.9 P = 2.3E−009 | 67.3 ± 7.3 | 10.4 ± 2.5 P = 0.03 | 9.4 ± 0.99 | 0.6 ± 0.4 P = 0.47 | 0.54 ± 0.35 |

TB drugs used in this arm are abbreviated as follows: Isoniazid (H), Rifampicin (R), Pyrazinamide (Z), Ethambutol (E), Streptomycin (S), Ofloxacin (O), Amikacin (A), Capreomycin (C), Para-aminosalicylic acid (Pas), Cs (Cycloserine), Cilastatin (Ci), Gatifloxacin (G), Metronidazole (F), Prothionamide (Pt)

TABLE 5

Baseline and outcome characteristics of TB patients receiving placebo in combination with TB drugs for 30 days

| No./Case No. | Sex | Age | Months on ATT prior to placebo | Dx | TB drugs regimen | Smear status | | Liver size in cm over normal | | Erythrocyte sedimentation rate (mm/h) | | Lymphocytes (%) | |
|---|---|---|---|---|---|---|---|---|---|---|---|---|---|
| | | | | | | before | after | before | after | before | After | Before | after |
| 1/191 | M | 22 | 1 | 1$^{st}$ Dx | HRZSE | 1 | 1 | 1 | 0 | 3 | 6 | 22 | 36 |
| 2/215 | F | 35 | 0 | 1$^{st}$ Dx | HRZSE | 3 | 3 | 1 | 0 | 22 | 41 | 8 | 10 |
| 3/234 | M | 40 | 0 | 1$^{st}$ Dx | HRZSE | 1 | 1 | 0 | 1 | 35 | 32 | 12 | 11 |
| 4/239 | F | 30 | 0 | 1$^{st}$ Dx | HRZSE | 1 | 1 | 0 | 1 | 8 | 10 | 21 | 16 |
| 5/227 | M | 20 | 0 | 1$^{st}$ Dx | HRZSE | 3 | 3 | 0 | 0 | 50 | 35 | 27 | 26 |
| 6/149 | M | 53 | 2 | RTB | HRZSE | 2 | 1 | 2 | 1 | 23 | 27 | 19 | 23 |
| 7/242 | M | 42 | 0 | RTB | HRZSE | 3 | 3 | 1 | 1 | 52 | 49 | 19 | 17 |
| 8/236 | M | 48 | 0 | RTB | HRZSE | 3 | 3 | 0 | 0 | 47 | 38 | 40 | 37 |
| 9/189 | M | 22 | 1 | MDR | HRZSE | 1 | 1 | 1 | 1 | 31 | 20 | 17 | 13 |
| 10/136 | M | 36 | 1 | MDR | ZAPas PtO | 1 | 1 | 3 | 3 | 33 | 30 | 27 | 25 |
| | | Mean 34.8 ± 3.58 Median 35.5 | Mean 0.5 ± 0.7 Median 0 | | | 1.9 P = 0.34 | 1.8 | 0.9 ± 0.31 P = 0.68 | 0.8 ± 0.29 | 30.4 ± 5.30 P = 0.61 | 28.8 ± 4.27 | 21.2 ± 8.9 P = 0.91 | 21.4 ± 9.7 |

TABLE 5-continued

Baseline and outcome characteristics of TB patients receiving placebo in combination with TB drugs for 30 days

| No./Case No. | Leukocyte count (×10⁹/L) before | after | Hb (g/L) Before | after | Weight change (kg) before | after | Total bilirubin (μmol/L) before | after | ALT (mM/h/ml) before | After |
|---|---|---|---|---|---|---|---|---|---|---|
| 1/191 | 6.1 | 8.7 | 155 | 150 | 74 | 75 | 12.1 | 9.9 | 0.3 | 0.3 |
| 2/215 | 8 | 14.1 | 75 | 80 | 45 | 45 | 8.8 | 8.8 | 0.4 | 0.6 |
| 3/234 | 11.8 | 11.1 | 158 | 150 | 62 | 62 | 9.9 | 9.9 | 0.4 | 0.6 |
| 4/239 | 7.2 | 7.4 | 126 | 120 | 69 | 69 | 8.8 | 14 | 0.2 | 0.6 |
| 5/227 | 9.2 | 10.9 | 116 | 110 | 64 | 66 | 8.8 | 8.8 | 0.3 | 0.2 |
| 6/149 | 5.5 | 4.6 | 86 | 89 | 84 | 86 | 12.1 | 8.8 | 0.3 | 0.1 |
| 7/242 | 10 | 9.8 | 113 | 115 | 60 | 61 | 8.8 | 8.8 | 0.1 | 0.4 |
| 8/236 | 11 | 10.3 | 139 | 129 | 60 | 61 | 8.8 | 17.2 | 0.1 | 0.4 |
| 9/189 | 8.8 | 7.7 | 136 | 146 | 70 | 72 | 8.8 | 8.8 | 0.4 | 0.6 |
| 10/136 | 10.1 | 9.1 | 107 | 131 | 69 | 69 | 21 | 12.1 | 0.7 | 1.7 |
|  | 8.77 ± 0.65 | 9.37 ± 0.80 | 121.1 ± 8.64 | 122 ± 7.69 | 65.7 ± 3.25 | 66.6 ± 3.39 | 10.79 ± 1.21 | 10.71 ± 0.90 | 0.32 ± 0.05 | 0.55 ± 0.14 |
|  | P = 0.43 | | P = 0.79 | | P = 0.01 | | P = 0.96 | | P = 0.055 | |

TB drugs used in this arm are abbreviated as follows: Isoniazid (H), Rifampicin (R), Pyrazinamide (Z), Ethambutol (E), Streptomycin (S), Amikacin (A), Para-aminosalicylic acid (Pas), Prothionamide (Pt), Ofloxacin (O)

The findings in Tables 4 and 5 support previous clinical trials of vaccine demonstrating favorable outcome in TB patients (Tables 1-3). These studies report a range of beneficial effects including better quality of life, body weight gain, reversal of ATT-associated hepatotoxicity, reduced inflammation, faster deffervescence, and higher clearance rate of M. tuberculosis in sputum smears. Furthermore, the adjunct immunotherapy resulted in much shorter duration of treatment than among those who received standard ATT. The normalization of inflammatory indices is considered to have favorable effect on the course of the TB disease. Contrary to the outcome in placebo group the markers of inflammation such as elevated leukocyte counts and prolonged erythrocyte sedimentation rate have been significantly reduced in vaccine recipients. A favorable change in the blood picture is supported by the increase in total lymphocyte percentage among vaccine recipients, but not in the control group. The restoration of suppressed lymphocyte counts and decrease in leukocyte counts is associated with positive treatment outcome. Thus, changes in relative and absolute lymphocyte and leukocyte numbers hold promise as surrogate markers of treatment response.

The hepatotoxicity induced by anti-TB drugs has serious adverse consequences to treated patients and imposes limitations on treatment options. Addition of instant composition appeared to reduce baseline bilirubin and ALT levels, as well as the abnormal liver size when compared to placebo regimen. For this reason the use of vaccine in combination with ATT is advisable to prevent or reverse iatrogenic liver damage.

The immunotherapy has shown clear benefit in reversing body weight loss. The average gain in vaccine and placebo groups was 3.5 kg and 0.9 kg which is almost identical to the results of placebo controlled trial involving a comparable group of 55 TB patients, i.e., 3.4 kg (59.7±8 vs 63.1±9 kg; P=5.7E-007) and 1.07 kg (59.1±10 vs 60.1±10.4 kg; P=0.003) respectively. In contrast, the mean weight gain observed in the earlier conducted, open-label trial involving 20 patients with HIV-TB was 7.7 kg (P=4.6E-007). This almost two-fold discrepancy is perhaps due to the fact that all these patients had HIV infection—a condition that is associated with worsened wasting.

Conversion of sputum smear from positive to negative is a main indicator of the efficacy of anti-TB intervention. The vaccine accelerates and significantly enhances bacillary clearance as compared to control group on AU. The difference in outcome between placebo and vaccine recipients was also significant. In the prior placebo-controlled study the conversion in placebo arm was seen in 25% of patients while in this trial 0% converted.

The instant vaccine is shown to be safe and capable of reversing ATT-associated hepatotoxicity. In addition, vaccine seems to reduce the inflammation as evidenced by several hematological and biochemical markers. Weight gain and sputum smear conversion rate have been significantly enhanced as compared to conventional ATT. As evidenced by obtained improvements the combination of vaccine and ATT can shorten the duration of treatment.

Example 4

Prophylactic use. Pooled blood from latent or active M. tuberculosis carrying donors are hydrolyzed in their entirety, heat-inactivated, embedded into metal salt matrix and made into solid form tablets, which is then fed to Swiss mice at a dose equivalent to dose proven effective in therapeutic use. After one month the Swiss mice are challenged with wild-type H37Rv mycobacterium strain by aerosol inhalation. The analysis reveals that 12 out of 13 of vaccinated mice failed to develop the TB infection by not showing any detectable bacilli. In contrast, all unvaccinated mice in control group had shown acute TB infection. The difference in outcome between control and vaccinated groups is highly significant as tested by Fisher's 2×2 exact test. Thus, vaccination of mice with instant vaccine elicits the protective immune response resulting in prevention of TB infection. The same results are obtained when recombinant yeast expressing mycobacteria antigens and alloantigens is fed to mice instead of mycobacterium from natural source.

All publications, patents, and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. A tableted composition, to be administered orally into a host in need thereof, said composition consisting of three components: (1) at least one hydrolyzed and heat-inactivated antigen of a non-recombinant *mycobacterium*; (2) at least one hydrolyzed and heat-inactivated non-recombinant alloantigen derived from pooled blood of the same species as the host; and (3) a magnesium salt bound to the antigen and the alloantigen.

2. The composition of claim 1 wherein said at least one antigen of a *mycobacterium* is derived from non-recombinant strains of BCG, *Mycobacterium (M.) tuberculosis, M. avium, M. habana, M. abscessus, M. aurum, M. bovis, M. vaccae, M. africanum, M. chelonae, M. fortuitum, M. fuerthensis, M. gastri. M. goodi, M. gordonae, M. immunogenum, M. intracellulare, M. paratuberculosis, M. lufu, M. kansasii, M. lentiflavum, M. leprae, M. w, M. mageritense, M. malmoense, M. marinum, M. massiliense, M. monacense, M. mucogenicum, M. neoaurum, M. peregrinum, M. phlei, M. porcinum, M. septicum, M. simiae, M. smegmatis, M. szulgai, M. terrae, M. tusciae, M. nonchromogenicum, M. ulcerans, M. chelonei, M. scrofulaceum, M. triviale, M. asciaticum, M. flavescens, M. genavense*, or *M.* xenopi.

* * * * *